US006008408A

United States Patent [19]
Denis et al.

[11] Patent Number: 6,008,408
[45] Date of Patent: *Dec. 28, 1999

[54] PROCESS FOR THE HYDROXYCARBONYLATION OF PENTENOIC ACIDS

[75] Inventors: Philippe Denis, Décines; Francois Klinger, Chaponost; Jean-Claude Laurent, Tassin-la-Demi-Lune; Robert Perron, Charly; Joël Schwartz, Caluire; Francois Vachet, Décines, all of France

[73] Assignee: Rhone-Poulenc Chimie, Courbevoie Cedex, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/424,335
[22] PCT Filed: Oct. 19, 1993
[86] PCT No.: PCT/FR93/01028
 § 371 Date: Jul. 11, 1995
 § 102(e) Date: Jul. 11, 1995
[87] PCT Pub. No.: WO94/08939
 PCT Pub. Date: Apr. 28, 1994

[30] Foreign Application Priority Data

Oct. 22, 1992 [FR] France .................................... 92 12913

[51] Int. Cl.$^6$ ...................................................... C07C 51/14
[52] U.S. Cl. ............................................................. 562/517
[58] Field of Search ............................................... 562/517

[56] References Cited

U.S. PATENT DOCUMENTS 5,166,421 11/1992 Bruner, Jr. ............................... 562/522

OTHER PUBLICATIONS

1st International Flock Conference, St. Petersburg State University of Technology and Design, Nov. 3–4, 1993.

*Primary Examiner*—Samuel Barts
*Assistant Examiner*—Rosalynd Keys
*Attorney, Agent, or Firm*—Burns, Doane, Swecker & Mathis, L.L.P.

[57] ABSTRACT

The present invention relates to a process for the hydroxycarbonylation of pentenoic acids. By the process, one or a number of pentenoic acids are hydroxycarbonylated to adipic acid, by carbon monoxide and water, in the presence of a catalyst based on iridium and/or rhodium and of at least one iodinated promoter. The reaction mixture obtained is subjected to a refining operation, after having optionally been concentrated, making it possible to separate at least a part of the catalyst. The catalyst thus separated is recycled to an operation for the hydroxycarbonylation of pentenoic acids, of butadiene, or of butadiene derivatives.

17 Claims, No Drawings

PROCESS FOR THE HYDROXYCARBONYLATION OF PENTENOIC ACIDS

This application was filed on Oct. 19, 1993 as International Application No. PCT/FR93/01028.

The present invention relates to a process for the hydroxycarbonylation of pentenoic acids for the preparation of adipic acid, in the presence of a catalyst which is at least partly separated from the reaction mixture obtained after the hydroxycarbonylation and reused in a hydroxycarbonylation operation.

One of the most promising processes for the preparation of adipic acid consists in hydroxycarbonylating one or a number of pentenoic acids, especially 3-pentenoic acid and 4-pentenoic acid, using carbon monoxide and water, in the presence of a catalyst based on iridium, rhodium or their mixtures and of an iodinated promoter. Generally, the reaction is carried out in the liquid phase at a temperature from 50° C. to 300° C. and under a partial carbon monoxide pressure of a few bar. In order to envisage the industrial use of a process of this type, it is very obviously indispensable to be able to recycle at least part of the expensive catalyst used.

The subject of the present invention is specifically a process containing such a recycling.

Among the separation techniques which can be envisaged, distillation of the more volatile compounds of the reaction mixture resulting from the hydroxycarbonylation allows the catalyst to remain with the diacids formed. A subsequent distillation of these diacids at low vapour pressure makes it necessary to subject them, and the catalyst, to a prolonged heating at a relatively high temperature, capable of degrading them and making the catalyst partially or entirely inactive.

The crystallization technique requires a sufficient heat transfer to be provided and for the production of crystals of a requisite size to be filtered off to be possible. In addition, the maximum level of solids is limited to an upper value of the order of 30 to 40%. All this leads to a significant equipment volume and to the immobilization of an excessively large amount of very expensive catalyst.

The present invention proposes to solve the problem of the separation and recycling of the catalyst in the context of a process for the hydroxycarbonylation of pentenoic acids to adipic acid, by the use of the refining technique.

More particularly, the subject of the invention is a process for the hydroxycarbonylation of pentenoic acids, characterized in that:
  one or a number of pentenoic acids are hydroxycarbonylated to adipic acid, by carbon monoxide and water, in the presence of a catalyst based on iridium and/or rhodium and of at least one iodinated promoter,
  the reaction mixture obtained is subjected to a refining operation, after having optionally been concentrated, making it possible to separate at least a part of the catalyst,
  the catalyst thus separated is recycled to an operation for the hydroxycarbonylation of pentenoic acids or of butadiene or of butadiene derivatives.

Pentenoic acid is understood to mean, in the context of the invention, 2-pentenoic acid, 3-pentenoic acid, 4-pentenoic acid and their mixtures.

3-Pentenoic acid, taken in isolation or as a mixture with its isomers, is more particularly suitable, owing to its accessability and the satisfactory results to which it leads during its hydroxycarbonylation.

The catalyst used for the hydroxycarbonylation reaction can be based on rhodium, iridium or both these metals.

Any rhodium or iridium source is capable of being used. Reference may be made, as examples of rhodium sources which can especially be used, to the compounds mentioned in European Patent EP-A-0,477,112, the contents of which are incorporated for reference in the present Patent Application.

Mention may be made, as examples of iridium sources which can especially be used, of:
  metallic Ir, $IrO_2$, $Ir_2O_3$,
  $IrCl_3$, $IrCl_3.3H_2O$,
  $IrBr_3$, $IrBr_3.3H_2O$,
  $IrI_3$,
  $Ir_2(CO)_4Cl_2$, $Ir_2(CO)_4I_2$,
  $Ir_2(CO)_8$, $Ir_4(CO)_{12}$,
  $Ir(CO)[P(C_6H_5)_3]_2I$,
  $Ir(CO)[P(C_6H_5)_3]_2Cl$,
  $Ir[P(C_6H_5)_3]_3I$,
  $HIr[P(C_6H_5)_3]_3(CO)$,
  $Ir(acac)(CO)_2$;
  $[IrCl(cod)]_2$,
  (cod=1,5-cyclooctadiene,
  acac=acetylacetonate).

The iridium-based catalyst which are more particularly suitable are: $[IrCl(cod)]_2$, $Ir_4(CO)_{12}$ and $Ir(acac)(CO)_2$.

The catalyst based on iridium or based on iridium and rhodium are particularly preferred in the context of the process of the invention.

The amount of catalyst to be used can vary within wide limits.

In general, an amount expressed in moles of metallic iridium and/or of metallic rhodium per liter of reaction mixture between $10^{-4}$ and $10^{-1}$ leads to satisfactory results. Lower amounts can be used: however, it is observed that the rate of reaction is low. Larger amounts have disadvantages only at the economic level.

The iridium and/or rhodium concentration is preferably between $5 \cdot 10^{-4}$ and $10^{-2}$ mol/liter.

Iodinated promoter is understood to mean, in the context of the process of the invention, HI and the organoiodinated compounds capable of generating HI under the reaction conditions and more particularly the alkyl iodides having 1 to 10 carbon atoms. Methyl iodide is more particularly recommended.

The amount of iodinated promoter to be used is generally such that the I/Ir (and/or Rh) molar ratio is greater than or equal to 0.1 It is not desirable that this ratio exceeds 20. The I/Ir (and/or Rh) molar ratio is preferably between 1 and 5.

The presence of water is indispensable to carrying out the hydroxycarbonylation. Generally, the amount of water to be used is such that the water/pentenoic acids molar ratio is between 0.01 and 10.

A larger amount is not desirable due to the loss in catalytic activity observed. The water/pentenoic acids molar ratio in the reaction mixture can be instantaneously less than the minimum value indicated above, if the reaction is carried out, for example, with continuous injection of water, rather than introducing it with the other charges before the hydroxycarbonylation reaction.

The water/pentenoic acids molar ratio is preferably between 0.01 and 1, the preceding comment regarding the minimum value also being valid.

The hydroxycarbonylation reaction can be carried out either in a third solvent or in a large excess of pentenoic acids.

It is possible to use, as third solvent, especially the saturated aliphatic or aromatic carboxylic acids containing at most 20 carbon atoms provided that they are liquid under the reaction conditions. There may be mentioned, as examples of such carboxylic acids, acetic acid, propionic acid, butyric acid, valeric acid, adipic acid, benzoic acid and phenylacetic acid.

The third solvent can also be chosen from saturated aliphatic or cycloaliphatic hydrocarbons and their chlorinated derivatives and aromatic hydrocarbons and their chlorinated derivatives, provided that these compounds are liquid under the reaction conditions. There may be mentioned, as examples of such solvents, benzene, toluene, chlorobenzene, dichloromethane, hexane and cyclohexane.

When it is present in the reaction mixture, the third solvent represents, for example, from 10% to 99% by volume with respect to the total volume of the said reaction mixture and preferably from 30% to 90% by volume.

According to a preferential variant, the hydroxycarbonylation reaction is carried out in the pentenoic acid themselves, that is to say 2-pentenoic acid, 3-pentenoic acid, 4-pentenoic acid and their mixtures.

The hydroxycarbonylation reaction is carried out at a pressure greater than atmospheric pressure and in the presence of carbon monoxide. It is possible to use essentially pure carbon monoxide or carbon monoxide of technical quality as it is found in commerce.

The reaction is carried out in the liquid phase. The temperature is generally between 100° C. and 240° C. and preferably between 160° C. and 200° C.

The total pressure can vary within wide limits. The carbon monoxide partial pressure, measured at 25° C., is generally from 0.5 bar to 50 bar and preferably from 1 bar to 25 bar.

The reaction mixture emerging from the hydroxycarbonylation reaction essentially contains the unreacted pentenoic acids, water, the iodinated promoter, the catalyst, the solvent optionally used, the adipic acid obtained, and the other by-products formed in more or less significant amounts, such as, for example, 2-methylglutaric acid, 2-ethylsuccinic acid, valeric acid or gamma-valerolactone (or 4-methylbutyrolactone).

This reaction mixture is subjected to a refining operation, either as such or preferably after a concentration operation, consisting in removing, especially by distillation, a part of or all the third solvent, if such a solvent was used, or a part of the excess pentenoic acids when the reaction was carried out without a third solvent. By such a concentration, the weight of the reaction mixture is generally reduced to a value representing from 10% to 90% of its initial weight, without these figures having a critical value.

Refining in the present text is defined as the direct crystallization of the reaction mixture, preferably concentrated, on a cooled wall, on which the raffinate (essentially adipic acid) is deposited, whereas the remaining liquid is concentrated in the other constituents of the treated mixture, including the catalyst. However, the crystal lattice deposited retains, by capillary attraction or inclusion, a limited amount of the residual liquid.

This technique is also known under the name of molten medium crystallization.

In the context of the process of the invention, the main object of the refining is to separate the majority of the adipic acid from the catalyst which remains essentially in the liquid residue (draw-off); for this, an apparatus is chosen which has a high heat exchange surface area/volume of reaction mixture to be treated ratio, so as to limit the duration of crystallization of the raffinate and especially the time the reaction mixture spends in the refiner and makes possible a degree of crystallization which can exceed 70%.

The refining operation can be described in the following general way.

The reaction mixture to be treated is introduced into the apparatus at an initial temperature at least equal to the crystallization temperature of the mixture and preferably between this temperature and the temperature at which the hydroxycarbonylation reaction was carried out; the apparatus is itself also at this temperature.

This initial temperature is generally between 100° C. and 200° C.

The first phase of the operation consists in the progressive crystallization of adipic acid on the walls of the apparatus. This crystallization is obtained by a programmed reduction in the temperature of the heat-exchange walls, especially using a heat-transfer fluid circulating on the other side of the said walls.

Depending on the type of industrial production envisaged, the temperature reduction can be more or less rapid, according to whether the mixture to be treated crystallizes in the relatively thin layer when it does not fill the whole volume of the apparatus or whether it crystallizes in forming a thick layer when the charged mixture is immobile and fills the whole volume of the apparatus.

The final temperature achieved is limited by the melting temperature of the eutectic of the various constituents of the reaction mixtures. It will be chosen according to the composition of the reaction mixture to be refined and according to the amount of adipic acid which it is desired to crystallize. As a general rule, the lower this temperature, the more certain other constituents of the reaction mixture risk contaminating the adipic acid crystals; conversely, the higher this temperature, the lower will be the degree of recovery of adipic acid in the raffinate.

Taking into account the above, the final temperature is generally fixed between 0° C. and 70° C.

When the final temperature chosen is achieved, the draining fraction, enriched in catalyst and impoverished in adipic acid with respect to the reaction mixture treated, is recovered by running from the lower part of the equipment. This constitutes the draining phase.

The third phase of the refining operation consists in washing the crystals deposited on the walls of the equipment, so as to recover the majority of the drained liquid still retained on the said crystals. It is carried out by reheating the deposited crystals, at a rate which varies depending on the type of industrial production, which causes their partial melting; draining and replacement on the crystals of the drained liquid by a liquid much richer in adipic acid is thus produced. This phase is called sweating phase. Its quantitative significance depends on the amount of catalyst which it is desired to recover and conditions the purity and the degree of recovery of the adipic acid. The sweating fraction can be added to the fraction obtained during the draining phase or be subjected to another separation operation of its constituents by any technique, especially by refining.

The term draw-off denotes, in the present text, the part of the reaction mixture separated during the draining phase and/or the sweating phase.

The temperature to which the raffinate is brought during the sweating phase varies depending on the amount of catalyst which it is desired to recover or the amount of purified adipic acid which it is desired to obtain.

This temperature is generally between the final temperature of the draining phase and 150° C. It is preferably between 100° C. and 145° C.

The raffinate deposited on the walls of the equipment can then be recovered by rapid melting of the crystals.

The duration of the refining cycle, consisting of these various phases, can vary from approximately 1 hour to 30 hours, depending on the industrial technology adopted; thus, a dynamic thin-layer system, offering a large heat exchange surface area with respect to the volume to be treated, will require a much shorter duration than a static thick-layer system.

The draw-off, containing at least a part of the catalyst, iodinated promoter, unconverted pentenoic acids and more or less significant amounts of the various constituents of the treated reaction mixture, can be directly recycled to a hydroxycarbonylation reaction (especially the draining fraction), or the subjected beforehand to one or a number of separation operations, targeting the separation of the catalyst from all or part of the other constituents (especially the sweating fraction). This additional separation can itself be carried out by the refining technique; however, it can be carried out by any other conventional technique such as, for example, crystallization, distillation, extraction.

The raffinate, largely containing adipic acid as well as the catalyst and more or less significant amounts of the various constituents of the treated reaction mixture, can be itself subjected to one or a number of additional separation operations, in order to separate the catalyst and the iodinated promoter which it contains. As indicated above for the draw-off, this additional separation can itself be carried out by the refining technique; however, it can be carried out by any other conventional technique such as, for example, crystallization, distillation, extraction. The catalyst and the iodinated promoter thus separated can then optionally be recycled.

The refining is carried out so that at least 40%, and preferably at least 80%, of the catalyst present in the reaction mixture to be treated is separated.

A preferential method of the invention consists in carrying out a refining operation, during which at least 80% of the catalyst is separated, between an initial temperature between 100° C. and 200° C. and a final temperature for the draining phase between 20° C. and 60° C., the temperature then being raised to between 100° C. and 145° C. for the sweating phase; this refining operation is optionally followed by one or a number of other separation operations carried out on some or all of the fractions obtained in order to separate the remainder of the catalyst, on the one hand, and at least a part of the branched diacids, on the other hand. The catalyst thus obtained during the refining is recycled to the hydroxycarbonylation reaction.

When the catalyst separated by the refining operation is used for the hydroxycarbonylation of butadiene or of its derivatives, there will be used, for example, the technique described for rhodium in Patent EP-A-0,405,433 and EP-A-0,274,076.

Besides butadiene, its derivatives which are the most generally usable are 3-buten-2-ol, 2-buten-1-ol, their mixtures and their carboxylic esters, especially the acetates, propionates, valerates, adipates and pentenoates.

The examples which follow illustrate the invention.

EXAMPLE 1

Hydroxycarbonylation of 3-Pentenoic Acid

The following are introduced into an autoclave equipped with stirring by a self-priming turbine:

2.45 g (7.3 mmol) of Ir in the form of $[IrCl(cod)]_2$ (3.3 mmol/l of reaction mixture)

4.17 g (18.6 mmol) of HI in the form of a 57% in weight for weight aqueous solution (8.4 mmol/l)

177.8 g (9.9 mol) of water (4.5 mmol/l)

2084 g (20.84 mol) of 3-pentenoic acid (P3).

The autoclave, connected to the gas supply under pressure, is hermetically closed. 2 bar (0.2 MPa) of CO are admitted while cold and heating is carried out to 185° C. over 20 min via an electric band heater. When this temperature is achieved, the pressure is adjusted to 20 bar (2 MPa).

The kinetics of the reaction are monitored by the absorption of CO in a reserve connected to the reactor, the pressure in the autoclave remaining constant.

After a reaction duration of 30 min, corresponding to the complete consumption of the introduced water, the reaction is halted by cooling the reaction mixture. The autoclave is degassed and the reaction mixture is drawn off in the liquid state at 120° C.

The reaction mixture is analysed by vapour phase chromatography and by high performance liquid chromatography.

| | |
|---|---|
| degree of conversion (DC) of P3: | 51% |
| molar yield with respect to converted P3 (Yd.) of adipic acid (A1): | 65% |
| Yd. of methylglutaric acid (A2): | 11% |
| Yd. of ethylsuccinic acid (A3): | 3% |
| Yd. of gamma-valerolactone (VAL): | 11% |
| Yd. of valeric acid (Pa): | 2% |
| Yd. of 2-pentenoic acid (P2): | 8% |

The degree of linearity, expressed by the ratio in percentage of A1 formed to all the diacids A1, A2 and A3 formed, is 82%.

The rate of reaction (calculated over 20 min of absorption of CO) is 5.4 mol of CO absorbed per hour and per liter of reaction mixture.

The reaction mixture is concentrated by distillation of the volatile products at 90° C. under a pressure of 1 kPa; a mixture is thus obtained which is subjected to a refining operation.

EXAMPLE 2

Refining of the Concentrated Reaction Mixture Prepared in Example 1

The apparatus used consists of a metal cylinder, with an internal diameter of 45 mm and a height of 65 cm, closed at its base by a small-volume pneumatic valve and equipped at its top with a screw-on lid through which two temperature probes and a nitrogen inlet pass.

The assembly is surrounded by a double jacket making possible the arranged circulation of a heat-transfer fluid at a controlled temperature.

1058 g of the concentrated reaction mixture prepared in Example 1, and which has the composition by weight given below, are used:

| | |
|---|---|
| adipic acid | 66.00% |
| 2-methylglutaric acid | 11.20% |
| 2-ethylsuccinic acid | 2.00% |
| gamma-valerolactone | 1.80% |
| 2-pentenoic acid | 3.00% |
| 3-pentenoic acid | 14.50% |
| 4-pentenoic acid | 1.30% |
| iridium (as a metal) | 0.0887% |
| iodine | 0.1565% |

This reaction mixture, in the liquid state at 131° C., is charged to the apparatus which is at this same temperature.

The temperature is progressively lowered using the heat-transfer fluid to 40° C. over 9 hours: this is the crystallization phase.

At 40° C., the valve of the apparatus is opened and the draining phase is carried out at a constant temperature for 3 h; the draining fraction, representing, in weight for weight, 20% of the reaction mixture charged, is thus recovered.

The temperature is then progressively raised to 138° C. over 11 h; during this sweating phase, a sweating fraction representing, in weight for weight, 28% of the reaction mixture charged, is recovered.

Finally, the temperature is brought, over 3 hours, to the melting temperature of the raffinate deposited on the walls of the apparatus and is maintained at this temperature for a further one hour. The raffinate is thus recovered which represents, in weight for weight, 52% of the reaction mixture charged.

The respective compositions of these three fractions are determined by assaying by gas phase chromatography, by high performance liquid chromatography and by X-ray fluorescence.

| Draining fraction: | |
|---|---|
| adipic acid | 10.0% |
| 2-methylglutaric acid | 32.0% |
| 2-ethylsuccinic acid | 5.4% |
| gamma-valerolactone | 8.4% |
| 2-pentenoic acid | 7.9% |
| 3-pentenoic acid | 33.5% |
| 4-pentenoic acid | 2.5% |
| iridium (as a metal) | 0.210% |
| iodine | 0.370% |
| Sweating fraction: | |
| adipic acid | 48.0% |
| 2-methylglutaric acid | 19.5% |
| 2-ethylsuccinic acid | 3.3% |
| gamma-valerolactone | 4.8% |
| 2-pentenoic acid | 5.5% |
| 3-pentenoic acid | 18.5% |
| 4-pentenoic acid | 0% |
| iridium (as a metal) | 0.133% |
| iodine | 0.228% |
| Raffinate: | |
| adipic acid | 95.8% |
| 2-methylglutaric acid | 2.2% |
| 2-ethylsuccinic acid | 0% |
| gamma-valerolactone | 0% |
| 2-pentenoic acid | 0% |
| 3-pentenoic acid | 2.0% |
| 4-pentenoic acid | 0% |
| iridium (as a metal) | 0.0149% |
| iodine | 0.0264% |

The raffinate thus contains 76% of the adipic acid and only 9% of the iridium and the iodine present in the reaction mixture emerging from the hydroxycarbonylation reaction.

The draining fraction contains 45% of the iridium and of the iodine and 3% of the adipic acid of the reaction mixture, whereas the sweating fraction contains 46% of the iridium and of the iodine and 21% of the adipic acid. Overall, the draw-off consisting of the combined draining and sweating fractions thus contains 91% of the iridium and of the iodine with 24% of the adipic acid of the reaction mixture. Different divisions of the fractions and raffinate make it possible either to minimize the amount of adipic acid present in the draw-off or to increase the degree of recovery of the iridium and the iodine depending on the favoured separation criterion.

EXAMPLE 3

Recycling of the Draining Fraction Obtained in Example 2 to a Hydroxycarbonylation Reaction 100 g of the draining fraction obtained in Example 2 are recycled. 3-Pentenoic acid and water are added to it so as to have an initial reaction mixture having the same concentration of Ir and of HI as the initial mixture used in Example 1, that is to say 3.3 mmol/l of Ir and 8.5 mmol/l of HI.

The concentrations in the initial mixture of the other constituents are the following:

7 mmol/l of P3
0.2 mmol/l of P2
0.04 mmol/l of P4
0.24 mmol/l of VAL
0.18 mmol/l of A1
0.6 mmol/l of A2
0.1 mmol/l of A3
4.2 mmol/l of water.

The hydroxycarbonylation is carried out as described in Example 1. After reacting for 40 min, corresponding to the consumption of the introduced water, the autoclave is cooled and the various constituents of the final reaction mixture are assayed.

The following results are obtained:

| | |
|---|---|
| degree of conversion (DC) of P3: | 58% |
| Yd. of adipic acid (A1): | 65% |
| Yd. of methylglutaric acid (A2): | 13% |
| Yd. of ethylsuccinic acid (A3): | 3% |
| Yd. of gamma-valerolactone (VAL): | 9% |
| Yd. of valeric acid (Pa): | 3% |
| Yd. of 2-pentenoic acid (P2): | 7% |

The degree of linearity, expressed by the ratio in percentage of A1 formed to all the diacids A1, A2 and A3 formed, is 80%.

The rate of reaction (calculated over 20 min of absorption of CO) is 4.4 mol of CO absorbed per hour and per liter of reaction mixture. The kinetics being of the order of 1 with respect to P3, the catalyst thus has an activity identical to that observed in Example 1 (absorption volume of CO/amount of P3 involved).

We claim:

1. Process for the hydroxycarbonylation of pentenoic acids, wherein:
   one or a number of pentenoic acids are hydroxycarbonylated to adipic acid, by carbon monoxide and water, in the presence of a catalyst based on iridium and/or rhodium and of at least one iodinated promoter,
   the reaction mixture obtained is subjected to a refining operation, after having optionally been concentrated, making it possible to separate at least a part of the catalyst, said refining operation comprising direct crystallization of the reaction mixture on a cooled wall on which adipic acid is deposited while concentrating the catalyst in the residual reaction mixture,
   the catalyst thus separated is recycled to an operation for the hydroxycarbonylation of pentenoic acids.

2. Process for the hydroxycarbonylation of pentenoic acids, wherein:
   one or a number of pentenoic acids are hydroxycarbonylated to adipic acid, by carbon monoxide and water, in the presence of a catalyst based on iridium and/or rhodium and of at least one iodinated promoter, the reaction mixture obtained is subjected to a refining operation, after having optionally been concentrated, making it possible to separate at least a part of the catalyst, said refining operation comprising direct crystallization of the reaction mixture on a cooled wall on which adipic acid is deposited while concentrating the catalyst in the residual reaction mixture, the catalyst thus separated is recycled to an operation for the hydroxycarbonylation of butadiene and/or of its derivatives.

3. Process according to claim 1, wherein at least 40% of the weight of the catalyst contained in the reaction mixture is separated by the refining operation.

4. Process according to claim 1, wherein the reaction mixture obtained after the hydroxycarbonylation operation is concentrated before being subjected to the refining operation in order to eliminate at least a part of the more volatile compounds which it contains.

5. Process according to claim 4, wherein the concentrate of the reaction mixture subjected to the refining operation represents, in weight by weight, from 10% to 90% of the reaction mixture emerging from the hydroxycarbonylation operation.

6. Process according to claim 1, wherein the hydroxycarbonylation is carried out in a solvent selected from the group consisting of saturated aliphatic or aromatic carboxylic acids having at most 20 carbon atoms, saturated aliphatic or cycloaliphatic hydrocarbons and their halogenated derivatives, aromatic hydrocarbons and their halogenated derivatives and aliphatic, aromatic or mixed ethers.

7. Process according to claim 1, wherein the hydroxycarbonylation is carried out in the pentenoic acids themselves.

8. Process according to claim 1, wherein the refining consists in cooling the optionally concentrated reaction mixture in a controlled and progressive way from an initial temperature at least equal to the crystallization temperature of the mixture, to a final temperature greater than or equal to the melting point of the eutectic of the constituents of the said reaction mixture, so as progressively to crystallize the adipic acid of the reaction mixture.

9. Process according to claim 8, wherein the initial temperature is between 100° C. and 200° C. and the final temperature between 0° C. and 70° C.

10. Process according to claim 1, wherein the refining contains a second phase, or draining phase, making it possible to separate at least a part of the catalyst within a draining fraction.

11. Process according to claim 1, wherein the refining contains a third phase, or sweating phase, consisting, by progressive heating of the deposited crystals, in recovering a sweating fraction containing another part of the catalyst and other constituents of the treated reaction mixture.

12. Process according to claim 11, wherein the sweating phase is carried out by heating at a temperature between the final temperature of the draining phase and 150° C.

13. Process according to claim 1, wherein the duration of the refining cycle varies between 1 hour and 30 hour.

14. Process according to claim 1, wherein the fraction obtained in the draining phase is recycled to the hydroxycarbonylation reaction.

15. Process according to claim 1, wherein the fractions obtained in the draining and sweating phases are recycled to the hydroxycarbonylation reaction.

16. The process according to claim 1, wherein at least 80% of the weight of the catalyst contained in the reaction mixture is separated by the refining operation.

17. The process according to claim 11, wherein the sweating phase is carried out by heating at a temperature between 100° C. and 145° C.

* * * * *